United States Patent
Bornzin et al.

(10) Patent No.: US 7,856,266 B1
(45) Date of Patent: Dec. 21, 2010

(54) IMPLANTABLE CARDIAC STIMULATION DEVICE PROVIDING REDUCED DEFIBRILLATION THRESHOLDS AND METHOD

(75) Inventors: Gene A. Bornzin, Simi Valley, CA (US);
Michael E. Benser, Valencia, CA (US);
Euljoon Park, Valencia, CA (US);
Taraneh Ghaffari Farazi, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 772 days.

(21) Appl. No.: 11/756,283

(22) Filed: May 31, 2007

(51) Int. Cl.
*A61N 1/39* (2006.01)
(52) U.S. Cl. .......................................................... 607/6
(58) Field of Classification Search ................ 607/4–5, 607/7, 46, 48, 63
See application file for complete search history.

(56) References Cited

U.S. PATENT DOCUMENTS

| | | | |
|---|---|---|---|
| 5,203,326 A | 4/1993 | Collins | |
| 5,314,448 A | 5/1994 | Kroll et al. | |
| 5,366,485 A | 11/1994 | Kroll et al. | |
| 7,158,826 B1 * | 1/2007 | Kroll et al. | 607/5 |
| 2004/0002739 A1 * | 1/2004 | Cates et al. | 607/6 |

FOREIGN PATENT DOCUMENTS

| | | |
|---|---|---|
| WO | 9701373 | 1/1997 |
| WO | 9709088 | 3/1997 |

OTHER PUBLICATIONS

Kolman, Benet S. MD et al., "The Effect of Vagus Nerve Stimulation upon Vulnerability of the Canine Ventricle," Circulation. Oct. 1975; 52(4):578-585.
Murakawa, Yuji MD et al., "Effect of Cervical Vagal Nerve Stimulatino on Defibrillation Energy," Jpn Heart J. Jan. 2003; 44(1): 91-100.

* cited by examiner

*Primary Examiner*—Niketa I Patel
*Assistant Examiner*—Rex Holmes

(57) ABSTRACT

An implantable cardiac defibrillation device provides pre-shock stimuli to reduce the defibrillation threshold (DFT). The device includes an arrhythmia detector that detects fibrillation of a fibrillating chamber of a heart and a pulse generator that provides a fibrillation therapy output responsive to the arrhythmia detector detecting fibrillation of the fibrillating chamber of the heart. The therapy output includes a defibrillating shock having an output magnitude exceeding a temporary defibrillation threshold of the fibrillating chamber and at least one pre-defibrillating shock output pulse that reduces an initial defibrillation threshold of the fibrillating chamber to the temporary defibrillation threshold. An electrode system having at least two defibrillation electrodes delivers both the at least one pre-defibrillating shock output pulse to the heart and the defibrillating shock to the fibrillating chamber of the heart.

12 Claims, 3 Drawing Sheets

IMPLANTABLE CARDIAC STIMULATION DEVICE PROVIDING REDUCED DEFIBRILLATION THRESHOLDS AND METHOD

FIELD OF THE INVENTION

The present invention is generally directed to an implantable cardiac stimulation device that provides defibrillation therapy. The present invention is more particularly directed to such a device that provides defibrillation threshold reduction stimulation prior to delivering a defibrillation shock.

BACKGROUND OF THE INVENTION

Implantable cardiac defibrillators (ICD's) are well known in the art. These devices, encapsulated in a conductive housing or enclosure, are generally implanted in a pectoral region of a patient and electrically connected to the heart with one or more electrode carrying leads. One lead includes at least one defibrillation electrode arranged to be positioned in the right ventricle. An arrhythmia detector detects ventricular arrhythmias, such as ventricular fibrillation. When such an arrhythmia is detected, a pulse generator delivers a defibrillating shock between the defibrillation electrode in the right ventricle and the conductive housing to terminate the fibrillation. Alternatively, such defibrillation devices may further include another defibrillation electrode arranged to be positioned in the right atrium or superior vena cava (SVC), hereinafter referred to as the SVC electrode, which may be electrically connected to the right ventricular defibrillation electrode. In this arrangement, the defibrillating shock is delivered between the commonly connected right ventricular and SVC electrodes and the conductive housing.

Ventricular fibrillation is an immediately life threatening cardiac arrhythmia. It requires immediate and effective defibrillation therapy. As a result, an ICD must be capable of providing a defibrillation shock having an output magnitude that is above the output level that is required to defibrillate the fibrillating heart chamber. This is known as the defibrillation threshold (DFT).

Being able to reduce the DFT is most desirable for a variety of reasons. First, all implanted devices, such as an ICD, are usually powered by a depletable power source, such as a battery. Reducing the DFT would thus serve to reduce the energy demands of the battery during defibrillation, thus extending the battery life. Also, the size of ICD's is largely dependent on the size of the battery. There is a constant desire to be able to make these devices smaller. If the energy requirements can be reduced as, for example, by reducing the DFT, the size of the battery and the ICD may ultimately be reduced. Most importantly, ICD's generally include a high voltage capacitor or capacitors that deliver the defibrillation shock. These capacitors must be first charged to the defibrillation output before the defibrillation shock can be administered. By lowering the DFT, the charge time of these capacitors may be reduced thus allowing the defibrillation therapy to be delivered more quickly. This is of course important because when a patient is experiencing a fibrillation episode, time is of the essence to preserve life. The present invention addresses this important issue of DFT reduction.

SUMMARY OF THE INVENTION

There is described an implantable cardiac stimulation device comprising an arrhythmia detector that detects fibrillation of a fibrillating chamber of a heart and a pulse generator that provides a fibrillation therapy output responsive to the arrhythmia detector detecting fibrillation of the fibrillating chamber of the heart. The fibrillation therapy output comprises a defibrillation shock having an output magnitude exceeding a temporary defibrillation threshold of the fibrillating chamber and at least one pre-defibrillating shock output pulse that reduces an initial defibrillation threshold of the fibrillating chamber to the temporary defibrillation threshold. The device further comprises an electrode system that delivers both the at least one pre-defibrillating shock output pulse to the heart and the defibrillating shock to the fibrillating chamber of the heart.

The at least one pre-defibrillating shock output pulse may have a duration of between fifty microseconds and one-hundred microseconds. The at least one pre-defibrillating shock output pulse may comprise a plurality of output pulses. Each of the plurality of pre-defibrillating shock output pulses may have a duration of between fifty microseconds and one-hundred microseconds.

The at least two defibrillation electrodes may comprise a first defibrillation electrode and a second defibrillation electrode. The first defibrillation electrode and the second defibrillation electrode may deliver the at least one pre-defibrillating shock output pulse to the heart. The first defibrillation electrode and the second defibrillation electrode may be arranged for implant in the superior vena cava of the heart and in the right ventricle of the heart.

The device may further comprise an electrically conductive enclosure and the first defibrillation electrode and the second defibrillation electrode may be the electrically conductive enclosure and an electrode arranged for implant in the right ventricle of the heart. Alternatively the first defibrillation electrode and the second defibrillation electrode may be the electrically conductive enclosure and an electrode arranged for implant in the superior vena cava of the heart.

The at least two defibrillation electrodes may alternatively comprise a first pair of defibrillation electrodes and a second pair of defibrillation electrodes, with the at least one pre-defibrillating shock output pulse being delivered by the first pair of defibrillating electrodes and the defibrillating shock being delivered by the second pair of defibrillating electrodes. The first pair of defibrillation electrodes and the second pair of defibrillation electrodes may share a common electrode.

The device may apply various different sequences of pulses to the heart while monitoring a characteristic of the heart related to the threshold reduction. The sequence of pulses providing the greatest reduction in defibrillation threshold may then be selected for the pre-defibrillation pulse therapy.

In another embodiment, an implantable cardiac stimulation device comprises an arrhythmia detector that detects fibrillation of a fibrillating chamber of a heart and a pulse generator that provides a fibrillation therapy output responsive to the arrhythmia detector detecting fibrillation of the fibrillating chamber of the heart. The fibrillation therapy output comprises a relatively high energy defibrillating shock having an output magnitude exceeding a temporary defibrillation threshold of the fibrillating chamber and at least one relatively low energy pre-shock output pulse provided prior to the relatively high energy defibrillating shock. The at least one relatively low energy pre-shock output pulse reduces an initial defibrillation threshold of the fibrillating chamber to the temporary defibrillation threshold. The device further includes a lead system having a plurality of defibrillation electrodes that deliver the relatively high energy defibrillating shock to the fibrillating chamber of the heart and wherein two of the plurality of defibrillation electrodes deliver the at least one relatively low energy pre-shock output pulse to the heart.

In another embodiment, a method for use in an implantable cardiac stimulation device comprises detecting fibrillation of a fibrillating chamber of a heart, responsive to detecting fibrillation of the fibrillating chamber of the heart, providing a fibrillation therapy output comprising a defibrillating shock having an output magnitude exceeding a temporary defibrillation threshold of the fibrillating chamber and at least one pre-defibrillating shock output pulse that reduces an initial defibrillation threshold of the fibrillating chamber to the temporary defibrillation threshold, and delivering both the at least one pre-defibrillating shock output pulse to the heart and the defibrillating shock to the fibrillating chamber of the heart through defibrillation electrodes.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
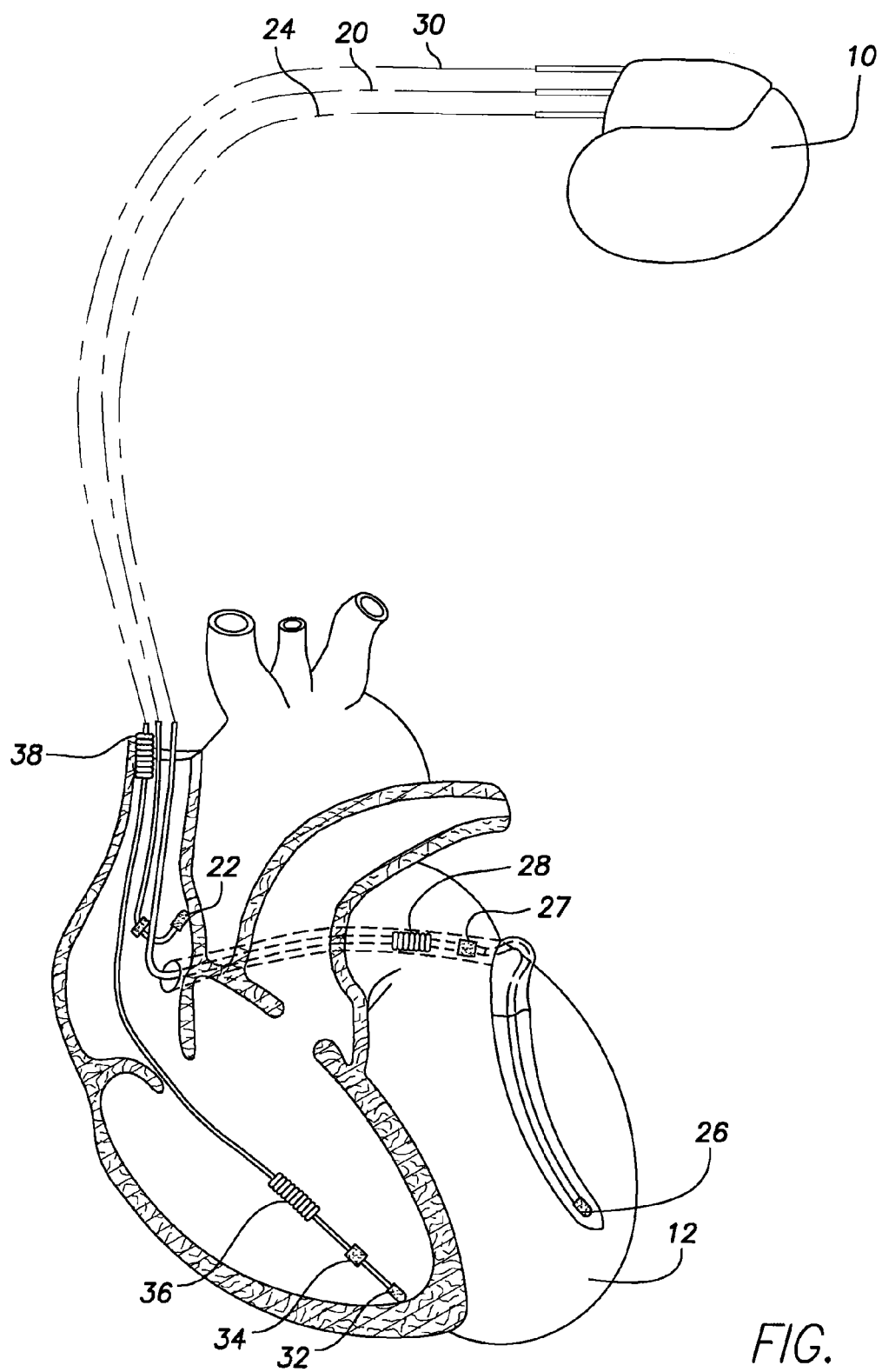
FIG. 1 is a simplified diagram illustrating an implantable cardiac defibrillation assembly embodying the present invention including an implantable cardiac stimulation device having defibrillation capability and a lead system including three leads implanted into a patient's heart for delivering multi-chamber pacing and defibrillation therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 by a lead connector 21. The lead 20 has at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 by a lead connector 25. The lead 24 is designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30. In this embodiment, the lead 30 includes a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
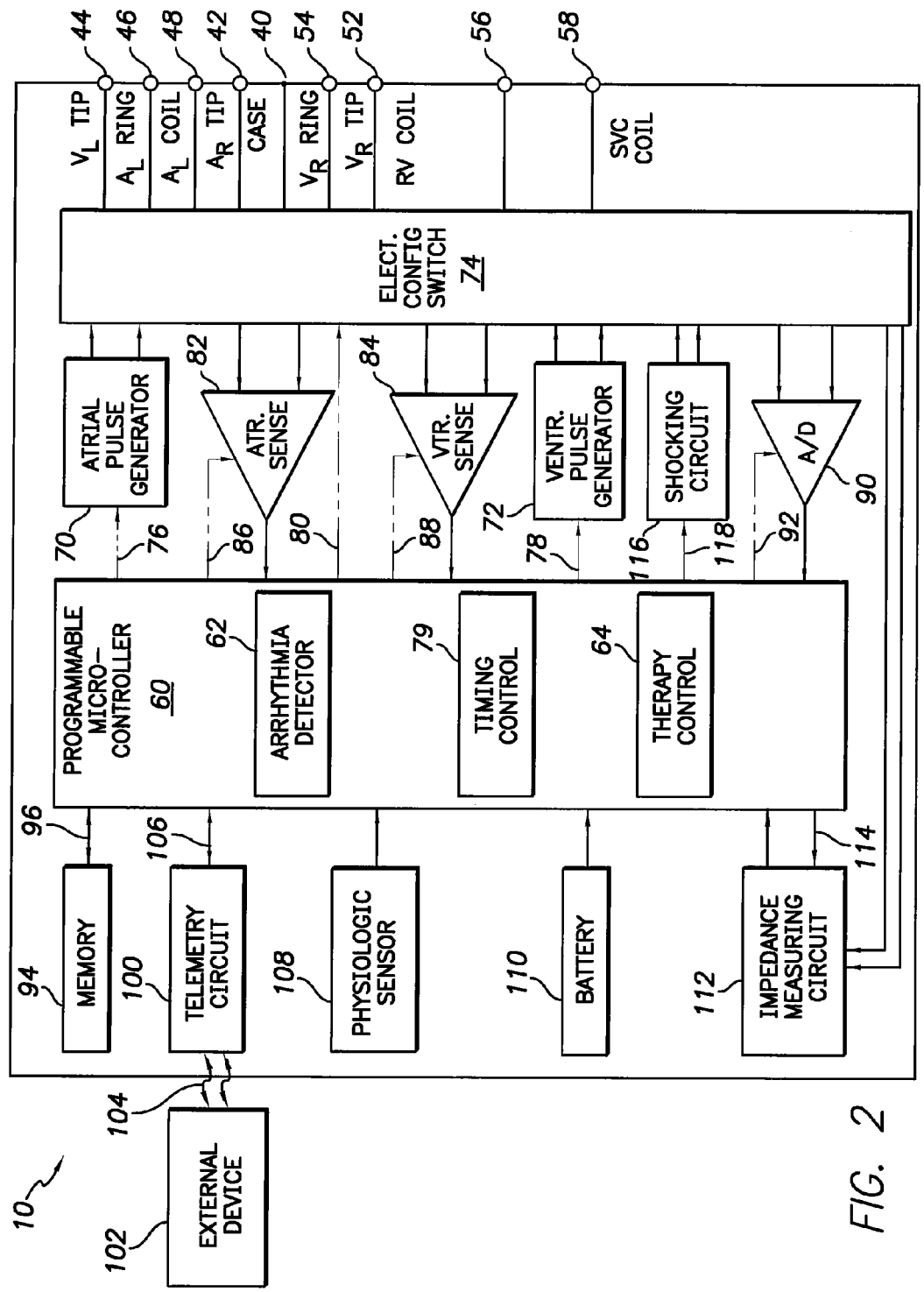
FIG. 2 is a functional block diagram of the implantable stimulation device illustrating the basic elements thereof for providing cardioversion, defibrillation and pacing stimulation in four chambers of the heart and defibrillation threshold reduction according to a embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown in FIG. 1 and schematically in FIG. 2, is often referred to as the "can", "case" or "case electrode" and may be programmably selected to act as a return electrode for all "unipolar" pacing modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, escape interval, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 includes an arrhythmia detector 62. It utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Lithium/silver vanadium oxide batteries have been found to be suitable for these purposes.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

In the case where the therapy to be provided by the stimulation device 10 is intended to include cardioversion and/or defibrillation, the device must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with the present invention, the device 10 is capable of providing a DFT reducing pulse or pulses prior to the delivery of a defibrillation shock. To that end, the device further includes a therapy control circuit 64. When fibrillation is detected by the arrhythmia detector 62, the therapy control causes the output capacitor of shocking circuit 116 to charge. After charging is complete or just at the point when charging is nearly complete, the therapy control 64 causes the shocking circuit 116 to provide one or more pre-defibrillation shock stimulation pulses to the heart using one of the possible defibrillation electrode combinations before the shocking circuit 116 provides the defibrillation shock. The device case 40 may also be used for this purpose. The one or more pre-shock stimulation pulses are designed to increase vagal input to the heart by stimulating cardiac efferent nerves in and/or around the heart. The pre-shock pulse or pulses comprise narrow stimuli having chronaxie times closely matching that of the efferent fibers. When the efferents are stimulated, the vagal tone of the heart increases and thus lowers the DFT.

The pre-shock pulse or pulses may be applied between the SVC coil electrode 38 and the case 40, the RV coil electrode 36 and the case 40, or the SVC coil electrode 38 and the RV coil electrode 36. The pre-shock pulses or pulses may thus be applied between the same defibrillation electrode combination used for the defibrillation shock pulse or a different combination of defibrillation electrodes. Hence, the pre-shock pulse or pulses may be applied between a first pair of defibrillation electrodes and the defibrillation shock may be applied between a different or second pair of electrodes. The first and second pair of defibrillation electrodes may however, share a common electrode.

Preferably, the pre-shock pulse or pulses have a duration of between about 50 (fifty) microseconds and 100 (one-hundred) microseconds. A single pre-shock pulse or a series of such narrow pre-shock pulses lasting up to three seconds and at a 15 to 100 Hz rate may be employed. The pulses may have a voltage of between 2 and 50 volts. Also preferably, these pulses may be provided at an early enough time with respect to the pending defibrillation shock to allow the reflex arc to be closed, i.e., enough time to activate afferent nervous fibers, for the information to be conducted centrally, and finally to activate vagal efferent fibers to reduce ventricular DFT. The pre-shock pulses are effective in reducing ventricular DFT because hyper-contractile states cause cardiac afferents to carry information centrally to trigger vagal mediated slowing during vasovagal syncope and stimulation of the cervical vagus reduces ventricular DFT's.

The pre-shock pulse or pulses will not significantly reduce the charge on the output capacitors because the pre-shock pulses are narrow. Hence, the pre-shock pulses are of relatively low energy while the defibrillation shock is of relatively high energy.

Figure 3:
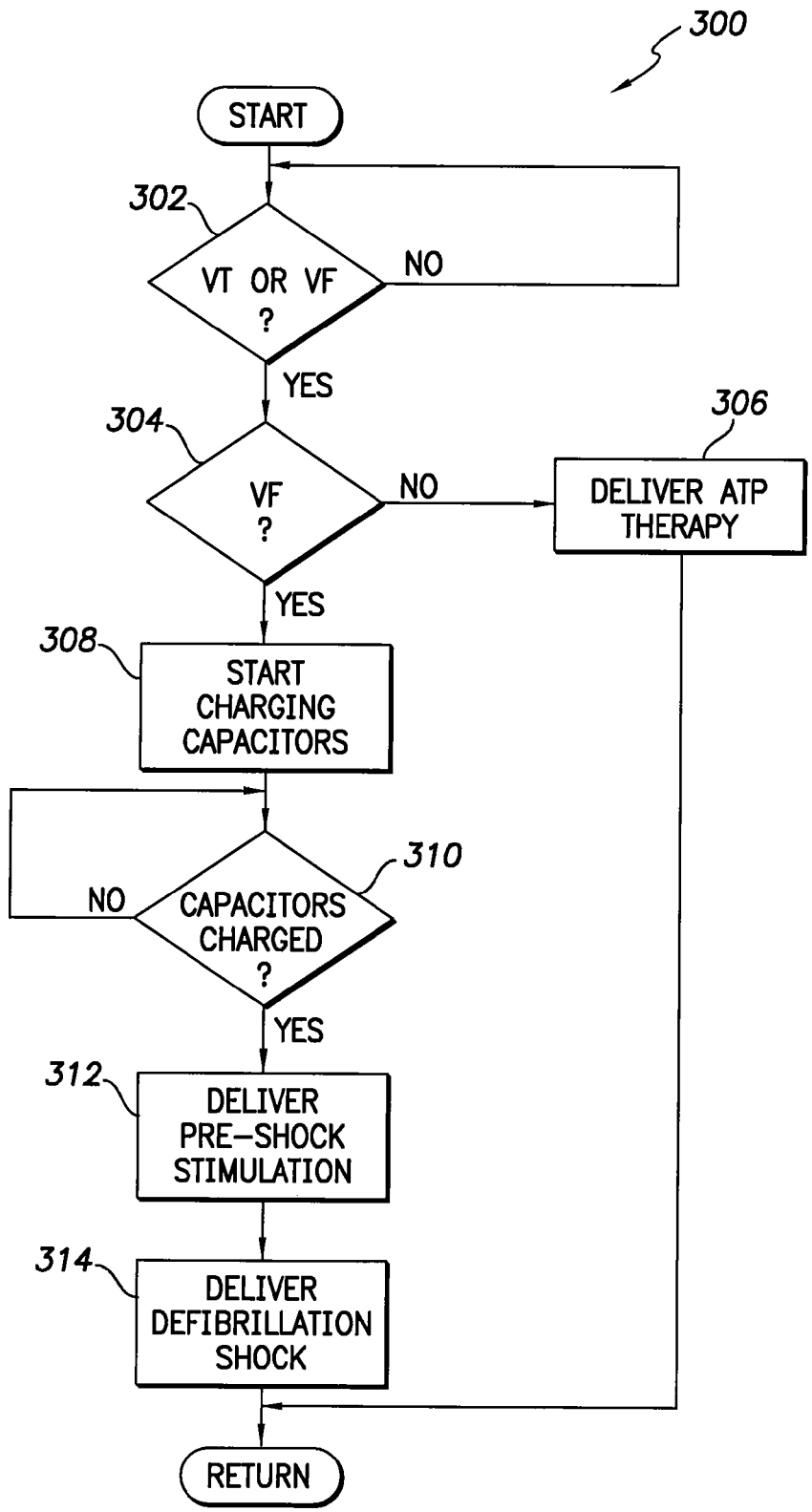
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process 300 of FIG. 3 initiates with decision block 302. Here, it is determined if the arrhythmia detector 62 has detected one of ventricular tachycardia (VT) and ventricular fibrillation (VF). If it has not, the process returns. If one of VT and VF is detected by the arrhythmia detector 62, the process advances to decision block 304 where it is determined if the detected arrhythmia is VF. If it is not, the detected arrhythmia must be VT. Accordingly, in that event, the process advances to activity block 306 where anti-tachycardia therapy, such anti-tachycardia pacing (ATP) is delivered to the ventricles. The process then returns.

If in decision block 304 it is determined that VF was detected, the process immediately advances to activity block 308 where charging of the output capacitors of shocking circuit 116 is begun. Then, the process advances to decision block 310 where the completion of capacitor charging is determined. When the output capacitors of the shocking circuit 116 are either nearly fully charged or fully charged, the process advances to activity block 312 where the therapy control 64 causes the shocking circuit to deliver the pre-shock pulse or pulses. The pre-shock pulse or pulses may be delivered as previously described. Once the pre-shock, DFT lowering pulse or pulses are applied, the ventricular DFT will be temporarily lowered from an initial threshold to a reduced threshold. The process then advances to activity block 314 where the therapy circuit 64 causes the shocking circuit to deliver the defibrillation shock while the heart has the temporarily lowered DFT. For this purpose, the therapy control 64 may cause the switch 74 to switch to a different defibrillation electrode combination or leave the switch 74 in its current condition to use the same defibrillation electrode combination for both the pre-shock DFT lowering stimuli and the final defibrillation shock. The process then returns.

The pre-defibrillating shock or shocks may be rendered most effective by the patient undergoing a test in order to determine what series of pre-defibrillating shock pulses is optimal for increasing the patient's vagal tone. This would render the greatest effect on reducing the defibrillation threshold. The test could be performed in the physician's office or clinic. Preferably, the therapy control 64 may initiate and coordinate the test so that the test may be performed automatically. To that end, the increased vagal tone may be monitored based on heart rate slowing or AV interval prolongation as various different sequences of pulses are applied to the heart. Such characteristics may also be monitored by the physician if a manual test is to be performed.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
a therapy control that causes different sequences of trains of pre-defibrillating shock output pulses to be applied to the heart; monitors a characteristic related to vagal tone as the different sequences of trains of pre-defibrillating shock output pulses are applied to the heart; and selects the pulse train of pre-defibrillating shock output pulses that result in increased vagal tone as a pre-defibrillating shock therapy to be provided in a defibrillation therapy, wherein the defibrillation therapy comprises the pre-defibrillating shock therapy followed by a defibrillating shock having a first energy;
an arrhythmia detector that detects fibrillation of a fibrillating chamber of a heart;
a pulse generator that provides the fibrillation therapy output responsive to the arrhythmia detector detecting fibrillation of the fibrillating chamber of the heart, wherein the pulse train of the pre-defibrillating shock therapy has a second energy lower than the first energy and a pulse duration of between fifty microseconds and one-hundred microseconds, wherein the pulses are provided at a rate of between 15-100 Hz; and
an electrode system that delivers both the pulse train of pre-defibrillating shock output pulses to the heart and the defibrillating shock to the fibrillating chamber of the heart.

2. The device of claim 1, wherein the electrode system comprises a first defibrillation electrode and a second defibrillation electrode, and wherein the first defibrillation electrode and the second defibrillation electrode deliver the pulse train of pre-defibrillating shock output pulses to the heart.

3. The device of claim 2, wherein the first defibrillation electrode and the second defibrillation electrode are an electrode arranged for implant in the superior vena cava of the heart and an electrode arranged for implant in the right ventricle of the heart.

4. The device of claim 2, further comprising an electrically conductive enclosure and wherein the first defibrillation electrode and the second defibrillation electrode are the electrically conductive enclosure and an electrode arranged for implant in the right ventricle of the heart.

5. The device of claim 2, further comprising an electrically conductive enclosure and wherein the first defibrillation electrode and the second defibrillation electrode are the electrically conductive enclosure and an electrode arranged for implant in the superior vena cava of the heart.

6. The device of claim 1, wherein the electrode system comprises a first pair of defibrillation electrodes and a second pair of defibrillation electrodes, and wherein the pulse train of pre-defibrillating shock output pulses is delivered by the first pair of defibrillating electrodes and the defibrillating shock is delivered by the second pair of defibrillating electrodes.

7. The device of claim 6, wherein the first pair of defibrillation electrodes and the second pair of defibrillation electrodes share a common electrode.

8. In an implantable cardiac stimulation device, a method comprising:
causing different sequences of trains of pre-defibrillating shock output pulses to be applied to the heart;
monitoring a characteristic related to vagal tone as the different sequences of trains of pre-defibrillating shock output pulses are applied to the heart;
selecting the train of pre-defibrillating shock output pulses that result in increased vagal tone as a pre-defibrillating shock therapy to be provided in a defibrillation therapy, wherein the defibrillation therapy comprises the pre-defibrillating shock therapy followed by a defibrillating shock having a first energy;
detecting fibrillation of a fibrillating chamber of a heart; and
responsive to detecting fibrillation of the fibrillating chamber of the heart, providing the fibrillation therapy; wherein the pulse train of the pre-defibrillating shock therapy has a second energy lower than the first energy and a pulse duration of between fifty microseconds and one-hundred microseconds, wherein the pulses are provided at a rate of between 15-100 Hz.

9. The method of claim 8, wherein providing the pulse train of pre-defibrillating shock output pulses comprises delivering an output pulse between a first defibrillation electrode in, on or near the heart and a second defibrillation electrode in, on or near the heart.

10. The method of claim 8, wherein providing a fibrillation therapy comprises delivering the pulse train of pre-defibrillating shock output pulses between a first defibrillation electrode within the superior vena cava of the heart and a second defibrillation electrode within the right ventricle of the heart.

11. The method of claim 8, wherein the device includes an electrically conductive enclosure and wherein providing a fibrillation therapy comprises delivering the pulse train of pre-defibrillating shock output pulses between the electrically conductive enclosure and a defibrillation electrode within the right ventricle of the heart.

12. The method of claim 8, wherein the device includes an electrically conductive enclosure and wherein providing a fibrillation therapy comprises delivering the pulse train of pre-defibrillating shock output pulses between the electrically conductive enclosure and a defibrillation electrode within the superior vena cava of the heart.

* * * * *